United States Patent [19]
Odorisio et al.

[11] Patent Number: 5,185,448
[45] Date of Patent: Feb. 9, 1993

[54] SUBSTITUTED 1-OXY-4-ACYLOXYPIPERIDINE AND 1-OXY-4-ACYLAMINOPIPERIDINE STABILIZERS

[75] Inventors: Paul A. Odorisio, Edgewater, N.J.; Sai P. Shum, Hawthorne, N.Y.

[73] Assignee: Ciba-Geigy Corporation, Ardsley, N.Y.

[21] Appl. No.: 697,134

[22] Filed: May 7, 1991

[51] Int. Cl.$^5$ .............. C07D 211/30; C07D 211/32
[52] U.S. Cl. ........................ 546/186; 546/190; 546/221; 546/223; 546/242; 546/244
[58] Field of Search ............ 546/186, 190, 221, 223, 546/242, 244

[56] References Cited

U.S. PATENT DOCUMENTS

| | | | |
|---|---|---|---|
| 3,507,876 | 4/1970 | McConnell | 546/244 |
| 3,644,278 | 2/1972 | Klemchuk | 524/100 |
| 4,316,996 | 2/1982 | Collonge et al. | 568/784 |
| 4,609,698 | 9/1986 | Karrer et al. | 546/150 |
| 4,668,721 | 5/1987 | Seltzer et al. | 524/95 |
| 4,782,105 | 11/1988 | Ravichandran et al. | 524/236 |
| 4,876,300 | 10/1989 | Seltzer et al. | 524/100 |
| 4,898,901 | 2/1990 | Ravichandran et al. | 524/237 |
| 5,006,577 | 4/1991 | Behreas | 546/186 |
| 5,015,683 | 5/1991 | Galbo | 546/186 |

OTHER PUBLICATIONS

A. R. Katrisky and C. W. Rees, Comprehensive Heterocyclic Chemistry, vol. 2, pp. 74, 95–96, 417–418 and 481 (1984).

Primary Examiner—C. Warren Ivy
Assistant Examiner—Celia Chang
Attorney, Agent, or Firm—Luther A. R. Hall

[57] ABSTRACT

Substituted 1-oxy-4-acyloxypiperidines or 1-oxy-4-acylaminopiperidines of formula I

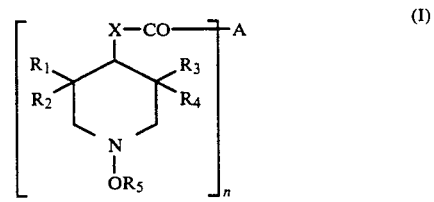

wherein $R_1$, $R_2$, $R_3$ and $R_4$ are independently hydrogen, alkyl or substituted alkyl, $R_5$ is hydrogen, alkyl, cycloalkyl, allyl or benzyl, X is —O— or —NE—, E is hydrogen, alkyl or cycloalkyl, A is an n-valent aliphatic or aromatic hydrocarbon radical, and n is 1 to 4 are effective in providing melt flow stabilization to polymeric materials during processing.

12 Claims, No Drawings

SUBSTITUTED 1-OXY-4-ACYLOXYPIPERIDINE AND 1-OXY-4-ACYLAMINOPIPERIDINE STABILIZERS

The present invention pertains to novel 1-oxy-4-acyloxypiperidines and 1-oxy-4-acylaminopiperidines and their use as stabilizers for various polymeric substrates during processing to provide superior melt flow stabilization.

BACKGROUND OF THE INVENTION

The substituted 1-oxy-4-acyloxypiperidines and 1-oxy-4-acylaminopiperidines are novel compounds as no examples of said compounds have been reported in the patent or the chemical literature.

1-Hydroxy(alkoxy)-2,2,6,6-tetramethyl-4-acyloxypiperidines and other 1-hydroxy(alkoxy)-2,2,6,6-tetramethylpiperidine derivatives are known as effective light stabilizers, but said compounds are not known to be particularly effective as processing stabilizers. Said compounds are also structurally distinguished from the instant compounds of this invention.

1-Hydroxy-2,6-dialkylpiperidines are disclosed to prevent discoloration of phenolic antioxidants in U.S. Pat. No. 4,316,996.

Substituted hydroxylamines, specifically N-hydroxypiperidine, are disclosed as effective antioxidants in U.S. Pat. No. 3,644,278.

Other structurally distinct hydroxylamines have been disclosed as processing stabilizers as seen in U.S. Pat. Nos. 4,668,721; 4,782,105; 4,876,300 and 4,898,901.

The instant compounds are structurally distinguished from each of the compounds disclosed in these prior art references and exhibit surprising superior process stabilization properties for polymeric substrates.

OBJECTS OF THE INVENTION

One object of the instant invention is to provide new substituted 1-oxy-4-acyloxypiperidines and 1-oxy-4-acylaminopiperidines which have superior process stabilizing properties for polymeric substrates.

Another object of the invention is to provide stabilized compositions containing the substituted 1-oxy-4-acyloxypiperidines and 1-oxy-4-acylaminopiperidines of this invention.

DETAILED DISCLOSURE

The instant invention pertains to novel substituted 1-oxy-4-acyloxypiperidines or 1-oxy-4-acylaminopiperidines of formula I

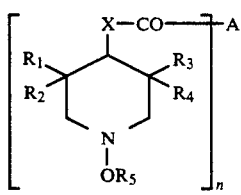

(I)

wherein $R_1$, $R_2$, $R_3$ and $R_4$ are independently hydrogen; a linear or branched alkyl of 1 to 30 carbon atoms; said alkyl optionally terminated with $-OR_6$, $-NR_7R_8$, $-SR_9$, $-COOR_{10}$ or $-CONR_{11}R_{12}$, where $R_6$, $R_7$, $R_8$, $R_9$ and $R_{10}$ are independently alkyl of 1 to 20 carbon atoms or alkenyl of 3 to 18 carbon atoms, and $R_{11}$ and $R_{12}$ are independently hydrogen or the same meaning as $R_6$; or said alkyl interrupted by one or more $-O-$, $-S-$, $-SO-$, $-SO_2-$, $-CO-$, $-COO-$, $-OCO-$, $-CONR_{13}-$, $-NR_{13}CO-$ or $-NR_{14}-$ where $R_{13}$ and $R_{14}$ have the same meaning as $R_{11}$; alkenyl of 3 to 20 carbon atoms; aryl of 6 to 10 carbon atoms; or said aryl substituted by one to three substituents selected from the group consisting of alkyl of 1 to 20 carbon atoms, cycloalkyl of 5 to 12 carbon atoms and phenylalkyl of 7 to 15 carbon atoms;

$R_5$ is hydrogen, alkyl of 1 to 18 carbon atoms, cycloalkyl of 5 to 12 carbon atoms, allyl or benzyl;

X is $-O-$ or $-NE-$,

E is hydrogen, alkyl of 1 to 18 carbon atoms or cycloalkyl of 5 to 12 carbon atoms, A is a direct bond; an n-valent linear or branched aliphatic hydrocarbon radical containing 1 to 20 carbon atoms, or said radical interrupted by one or more $-O-$, $-S-$, $-SO-$, $-SO_2-$, $-CO-$, $-COO-$, $-OCO-$, $-CONR_{15}-$, $-NR_{15}CO-$ or $-NR_{16}-$ where $R_{15}$ and $R_{16}$ have the same meaning as $R_{11}$; an n-valent aromatic or aromatic-aliphatic hydrocarbon of 6 to 30 carbon atoms, or said radical interrupted by one or more $-O-$, $-S-$, $-SO-$, $-SO_2-$, $-CO-$, $-COO-$, $-OCO-$, $-CONR_{17}$, $-NR_{17}CO-$ or $-NR_{18}-$ where $R_{17}$ and $R_{18}$ have the same meaning as $R_{11}$; and n is an integer of 1 to 4.

All possible geometric isomers and stereoisomers which are predictable are to be included in the scope of this invention.

Preferably $R_1$, $R_2$, $R_3$ and $R_4$ are independently hydrogen or methyl; most preferably hydrogen.

Preferably $R_5$ is hydrogen, allyl or benzyl.

Preferably n is 1 or 2.

Preferably X is $-O-$.

Preferably A is alkyl of 1 to 18 carbon atoms when n is 1; and alkylene of 2 to 12 carbon atoms when n is 2.

Most preferably A is alkyl of 11 to 17 carbon atoms when n is 1; and alkylene of 2 to 8 carbon atoms when n is 2.

Most preferably $R_5$ is hydrogen or allyl.

The instant invention also pertains to stabilized compositions containing an effective stabilizing amount of a compound of formula I as defined above.

The compounds of the instant invention are conveniently prepared by the reaction of a 4-hydroxypiperidine with an allyl halide, benzyl halide or lower alkyl acrylate followed by oxidation of the product formed with a peroxy compound, such as meta-chloroperbenzoic acid, to the corresponding 1-oxy compound. This is followed by a classic acylation of the 4-hydroxy group with an acid halide or acid anhydride.

The starting materials and intermediates used to make the instant compounds are largely items of commerce or can be made by methods known in the art.

The starting 4-hydroxypiperidines are obtained by reduction of the corresponding piperid-4-ones which in turn are readily accessible by classical synthetic methods as seen in A. R. Katritsky and C. W. Rees, Comprehensive Heterocyclic Chemistry, Vol. 2, pp 74, 95–96, 417–418 and 481 (1984); and Sir Derek Barton and W. D. Ollis, Comprehensive Organic Chemistry, Vol. 4, pp 42–43 and 64–65 (1979).

When any of $R_1$ to $R_{19}$, E or A is alkyl, such alkyl groups are, for example, methyl, ethyl, propyl, isopropyl, n-butyl, isobutyl, tert-butyl, tert-amyl, 2-ethylhexyl, n-octyl, undecyl, lauryl, heptadecyl, octadecyl, eicosyl and tricontyl; when said radicals, are alkenyl, they are, for example, allyl and oleyl; when said radicals are phenylalkyl, they are, for example, benzyl, phenethyl, α-methylbenzyl and α,α-dimethylbenzyl; when said radicals are aryl, they are, for example, phenyl, naphthyl, or when substituted by alkyl are, for example, tolyl and xylyl; when said radicals are alkyl interrupted by —O—, they are, for example, 3-oxaamyl and 3,6-dioxaoctyl; when A is alkylene, said alkylene interrupted by —O—, A is, for example, ethylene, trimethylene, tetramethylene, hexamethylene, octamethylene, 3-oxapentamethylene and 3,6-dioxaoctamethylene; then A is arylene, A is, for example, o-phenylene, m-phenylene, p-phenylene and naphthylene; when A is alkanetriyl, it is, for example, 1,2,3-propanetriyl; and when A is alkanetetryl, A is, for example, 1,2,3,4-butanetetryl.

The substituted 1-oxy-4-acyloxypiperidines of this invention exhibit surprising process stabilization properties distinct from that shown by prior art compounds.

The instant compounds are structurally distinct from prior art compounds. Their structures allow for the preparation of high molecular weight material of low volatility, enhanced compatibility with the substrate and low extractability. The instant compounds provide superior melt flow stabilization during polymer processing. The instant compounds also have superior hydrolytic stability over the state of the art phosphite stabilizers.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber; and lubricating oils.

In general polymers which can be stabilized include
1. Polymers of monoolefins and diolefins, for example polyethylene (which optionally can be crosslinked), polypropylene, polyisobutylene, polybutene-1, poly-methylpentene-1, polyisoprene or polybutadiene, as well as polymers of cycloolefins, for instance of cyclopentene or norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.
16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and melamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
  1.1. Alkylated monophenols, for example,
  2,6-di-tert-butyl-4-methylphenol
  2-tert.butyl-4,6-dimethylphenol
  2,6-di-tert-butyl-4-ethylphenol
  2,6-di-tert-butyl-4-n-butylphenol
  2,6-di-tert-butyl-4-i-butylphenol
  2,6-di-cyclopentyl-4-methylphenol
  2-($\alpha$-methylcyclohexyl)-4,6-dimethylphenol
  2,6-di-octadecyl-4-methylphenol
  2,4,6-tri-cyclohexylphenol
  2,6-di-tert-butyl-4-methoxymethylphenol.
  1.2. Alkylated hydroquinones, for example,
  2,6-di-tert-butyl-4-methoxyphenol
  2,5-di-tert-butyl-hydroquinone
  2,5-di-tert-amyl-hydroquinone
  2,6-diphenyl-4-octadecyloxyphenol.
  1.3. Hydroxylated thiodiphenyl ethers, for example,
  2,2'-thio-bis-(6-tert-butyl-4-methylphenol)
  2,2'-thio-bis-(4-octylphenol)
  4,4'-thio-bis-(6-tert-butyl-3-methylphenol)
  4,4'-thio-bis-(6-tert-butyl-2-methylphenol).
  1.4. Alkylidene-bisphenols, for example,
  2,2'-methylene-bis-(6-tert-butyl-4-methylphenol)
  2,2'-methylene-bis-(6-tert-butyl-4-ethylphenol)
  2,2'-methylene-bis-[4-methyl-6-($\alpha$-methylcyclohexyl)-phenol]
  2,2'-methylene-bis-(4-methyl-6-cyclohexylphenol)
  2,2'-methylene-bis-(6-nonyl-4-methylphenol)
  2,2'-methylene-bis-[6-($\alpha$-methylbenzyl)-4-nonylphenol]
  2,2'-methylene-bis-[6-($\alpha,\alpha$-dimethylbenzyl)-4-nonylphenol]
  2,2'-methylene-bis-(4,6-di-tert-butylphenol)
  2,2'-ethylidene-bis-(4,6-di-tert-butylphenol)
  2,2'-ethylidene-bis-(6-tert-butyl-4-isobutylphenol)
  4,4'-methylene-bis-(2,6-di-tert-butylphenol)
  4,4'-methylene-bis-(6-tert-butyl-2-methylphenol)
  1,1-bis-(5-tert-butyl-4-hydroxy-2-methylphenyl-butane
  2,6-di-(3-tert-butyl-5-methyl-2-hydroxybenzyl)-4-methylphenol
  1,1,3-tris-(5-tert-butyl-4-hydroxy-2-methylphenyl)-butane 1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt.

1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate.

1.7. Esters of β-(3,5-di-tert-butyl-4-hydroxyphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide.

1.8. Esters of β-(5-tert-butyl-4-hydroxy-3-methylphenyl)-propionic acid with monohydric or polyhydric alcohols, for example,
methanol
octadecanol
1,6-hexanediol
neopentyl glycol
thiodiethylene glycol
diethylene glycol
triethylene glycol
pentaerythritol
tris-hydroxyethyl isocyanurate
di-hydroxyethyl oxalic acid diamide.

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine.

1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis(3,3,5,5-tetramethylpiperazinone), bis(1-octyloxy-2,2,6,6-tetramethylpiperidin-4-yl) sebacate.

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2hydroxyethoxy)phenyl]-6-(4-bromophenyl)-s-triazine; 2,4-bis[2-hydroxy-4-(2-acetoxyethoxy)phenyl]-6-(4chlorophenyl)-s-triazine, 2,4-bis(2,4-dihydroxyphenyl)6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl, phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example, copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl) sebacate, bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]undecane) diethyl] 1,2,3,4-butanetetracarboxylate, mixed [1,2,2,6,6- pentamethylpiperidin-4-yl/β,β,β',β'-tetramethyl-3,9-(2,4,8,10-tetraoxaspiro[5.5]undecane)diethyl] 1,2,3,4-butanetetracarboxylate, octamethylene bis(2,2,6,6-tetramethylpiperidin-4-carboxylate), 4,4'-ethylenebis(2,2,6,6-tetramethylpiperazin-3-one) and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The following examples are presented for the purpose of illustration only and are not to be construed to limit the nature or scope of the instant invention in any manner whatsoever.

EXAMPLE 1

1-Allyl-4-hydroxypiperidine

Into a mixture of 4-hydroxypiperidine (75 g, 0.74 mol) and potassium carbonate (104 g, 0.75 mol) in ethanol (250 ml) is added allyl bromide (65 ml, 0.74 mol) in four equal portions over a three-hour period. After the addition is complete, the reaction mixture is stirred at ambient temperature until the disappearance of the reactants, as determined by TLC analysis (approximately six hours). The insoluble solids formed are then removed by filtration and the filtrate is concentrated in vacuo. The residue is purified by flash chromatography on silica gel with a mixture of 25% (vol.) methanol in ethyl acetate as the solvent to give 53.2 g (51% yield) of the title compound as a yellow oil.

$^{13}$CNMR (90 MHz)(Benzene-d6); (ppm); 136.2; 117.3; 66.9; 61.2; 51.1; 34.8.

EXAMPLE 2

1-Allyloxy-4-hydroxypiperidine

Into a solution of 1-allyl-4-hydroxypiperidine, prepared in Example 1, (5 g, 0.35 mol) in dichloromethane (50 ml) at -5° C. is added dropwise a solution of 85% active m-chloroperbenzoic acid (7.2 g, 0.35 mol) in dichloromethane (200 ml). After the addition is complete, the reaction mixture is warmed to ambient temperature with stirring. After two hours, the reaction mixture is concentrated in vacuo to give a red residue which is purified by flash chromatography on basic alumina with 40% (vol.) methanol in ethyl acetate as the solvent to give 2.5 g of a brown oil. The brown oil is dissolved into 10 ml of toluene and refluxed for 2.5 hours. The solution is concentrated in vacuo and resultant residue is purified by flash chromatography on silica gel with 25% (vol.) ethyl acetate in hexane as solvent to give 0.95 g (17% yield) of the title compound as a yellow oil.

$^1$HNMR (200 MHz)(Benzene-d6) (ppm); 1.5–2.0 (m, 5H); 2.72 (bs, 2H); 3.22 (m, 2H); 3.66 (m, 1H); 4.30 (d of t, 2H); 5.15 (d of d of t, 1H); 5.30 (m, 1H); 6.07 (q of t, 1H).

EXAMPLE 3

1-(2-Methoxycarbonyl)ethylpiperidin-4-yl Stearate

A mixture of 4-hydroxypiperidine (35.5 g, 0.35 mol) and methyl acrylate (30.1 g, 0.35 mol) is heated to 74° C. After five hours, excess methyl acrylate (6.0 g, 0.07 mol) is added to the reaction mixture. After an additional half hour at 74° C., unreacted methyl acrylate is removed in vacuo to give 66.9 g of crude yellowish oil. A mixture of the yellowish crude oil (12.35 g), ether (100 ml) and triethylamine (6.7 g, 8.80 ml, 0.07 mol) is added dropwise to a solution of stearoyl chloride (20 g, 0.07 mol) in ether (150 ml) at −5° C. After the addition is complete, the reaction mixture is allowed to warm to ambient temperature with stirring. The reaction is considered complete upon disappearance of the reactants as determined by inspection of the IR spectrum of an aliquot wherein the carbonyl stretch band of the stearoyl chloride at 1800 cm$^{-1}$ and the hydroxyl stretch band of the 4-hydroxypiperidine derivative at 3500 cm$^{-1}$ are absent. The precipitate which has formed is removed by filtration. The filtrate is concentrated in vacuo to give 32 g of the title compound as a pale yellow solid: m.p. 46°–50° C.

IR (CH$_2$Cl$_2$) 1740 cm$^{-1}$.

EXAMPLE 4

1-Hydroxypiperidin-4-yl Stearate

A mixture of 50% active m-chloroperbenzoic acid (9.8 g, 0.048 mol) and chloroform (130 ml) is added dropwise to a mixture of 1-(2-methoxycarbonyl)ethylpiperidin-4-yl stearate (22 g, 0.05 mol) and chloroform (130 ml) at 13° C. under nitrogen. Reaction is complete in four hours. Removal of solvent gives a yellowish crude residue which is purified by flash chromatography on basic alumina with ethyl acetate as solvent to give 4.6 g (25% yield) of the title compound as a white solid: m.p. 75°–80° C.

Analysis: Calcd. for C$_{23}$H$_{45}$NO$_3$: C, 72.0; H, 11.8; N, 3.6. Found: C, 71.7; H, 11.7; N, 3.5.

EXAMPLE 5

Bis[1-(2-methoxycarbonyl)ethylpiperidin-4-yl] Sebacate

The procedure of Example 3 is repeated using 18.7 g (0.1 mol) of 4-hydroxy-1-(2-methoxycarbonyl)ethylpiperidine, 10.1 mL (0.048 mol)of sebacoyl chloride, 14 mL (0.1 mol) of triethylamine and 240 mL of diethyl ether. The isolated reaction mixture is purified by flash chromatography (silica gel; 95:5 v/v ethyl acetate:methanol solvent) to give 14.9 g (58% yield) of the title compound as a white solid: mp 55°–59° C.

Analysis: Calcd. for C$_{28}$H$_{48}$N$_2$O$_8$: C, 62.2; H, 9.0; N, 5.2. Found: C, 62.4; H, 9.0; N, 5.1.

EXAMPLE 6

Bis(1-Hydroxypiperidin-4-yl) Sebacate

The procedure of Example 4 is repeated using 14 g (26 mmol) of bis[1-(2-methoxycarbonyl)ethylpiperidin-4-yl] sebacate, 10.5 g (52 mmol) of 85% active meta-chloroperbenzoic acid and 200 ml of ethyl acetate. The isolated reaction mixture is purified by HPLC (silica gel; 95:5 v/v ethyl acetate:methanol) followed by recrystallization from ethyl acetate to give 3.6 g (35% yield) of the title compound as a white solid: mp 133°–135° C.

Analysis: Calcd. for $C_{20}H_{36}N_2O_6$: C, 60.0; H, 9.1; N, 7.0. Found: C, 59.6; H, 8.9; N, 7.0.

EXAMPLE 7

Bis(1-allyloxy-3,5-dimethylpiperidin-4-yl) Sebacate

The general procedure of Example 3 is repeated using 1-allyloxy-3,5-dimethyl-4-hydroxypiperidine, sebacoyl chloride and triethylamine in diethyl ether solvent to give the title compound.

EXAMPLE 8

Bis(1-allyloxypiperidin-4-yl) Sebacate

Following the general procedure of Example 1 using bis(1-hydroxypiperidin-4-yl) sebacate, potassium carbonate and allyl bromide in ethanol solvent, the title compound is obtained.

EXAMPLE 9

1-Allyloxypiperidin-4-yl Stearate

Repeating the general procedure of Example 1 using 1-hydroxy-piperdin-4-yl stearate, potassium carbonate and allyl bromide in ethanol solvent yields the title compound.

EXAMPLE 10

Bis(1-benzyloxypiperidin-4-yl) Sebacate

The general procedure of Example 3 is repeated using 1-benzyloxy-4-hydroxypiperidine, sebacoyl chloride and triethylamine in diethyl ether solvent to give the title compound.

EXAMPLE 11

1-Benzyloxypiperidin-4-yl Stearate

The general procedure of Example 1 is repeated using 1-hydroxypiperidin-4-yl stearate, poassium carbonate and benzyl bromide in ethanol solvent to give the title compound.

EXAMPLE 12

4-(N-n-butyl-N-stearoylamino)-1-hydroxypiperidine

The general procedure of Example 4 is followed using 4-(n-butyl-N-stearoylamino)-1-(2-methoxycarbonyl)ethylpiperidine and 50% active m-chloroperbenzoic acid in chloroform to give the title compound.

EXAMPLE 13

Process Stabilization of Polypropylene at 525° F. (274° C.)

This example illustrates the process stabilizing effectiveness of the instant compounds in polypropylene.

The base formulation comprises unstabilized, old technology polypropylene (PROFAX 6501, Himont) containing 0.075% by weight of calcium stearate. The test additives are incorporated into the polypropylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion | |
|---|---|---|---|
| | | 1 | 5 |
| None | — | 10.5 | 61.7 |
| Phosphite 1 | 0.075 | 5.0 | 21.5 |
| Phosphite 2 | 0.075 | 3.1 | 4.5 |
| HA 1 | 0.075 | 3.2 | 7.4 |
| Compound of Example 6 | 0.075 | 2.9 | 6.1 |

*Phosphite 1 is tris(2,4-di-tert-butylphenyl)phosphite.
Phosphite 2 is bis(2,4-di-tert-butylphenyl)pentaerythrityl diphosphite.
HA 1 is N,N-dibenzylhydroxylamine.

These results show that the instant compounds provide superior melt flow stabilization to polypropylene during processing compared to the state of the art processing stabilizers.

EXAMPLE 14

Process Stabilization of Polypropylene at 525° F. (274° C.)

This example illustrates the process stabilizing efficacy of the instant compounds in polypropylene in formulations containing a phenolic antioxidant.

The results using the procedure described in Example 13 on polypropylene formulations containing an instant compound and a phenolic antioxidant are given in the table below.

| Additive* | Concentration (% by weight) | Melt Flow after Extrusion | |
|---|---|---|---|
| | | 1 | 5 |
| AO A | 0.075 | 6.7 | 20.2 |
| AO A plus Phosphite 1 | 0.075 0.075 | 3.6 | 7.0 |
| AO A plus HA 2 | 0.075 0.075 | 3.2 | 6.0 |
| AO A plus HA 1 | 0.075 0.075 | 5.2 | 13.6 |
| AO A plus Example 6 | 0.075 0.075 | 3.0 | 5.3 |

*AO A is neopentanetetrayl tetrakis(3,5-di-tert-butyl-4-hydroxyhydrocinnamate).
Phosphite 1 is tris(2,4-di-tert-butylphenyl)phosphite.
HA 2 is N,N-dioctadecylhydroxylamine.
HA 1 is N,N-dibenzylhydroxylamine.
Example 6 compound is bis(1-hydroxypiperidin-4-yl)sebacate.

These results show that the substituted 1-oxy-4-acyloxypiperidines in combination with a phenolic antioxidant provide melt flow stabilization to polypropylene during processing that is superior to that provided by the state of the art processing stabilizers.

EXAMPLE 15

Process Stabilization of Polypropylene at 536° F. (280° C.)

This example illustrates the process stabilizing effectiveness of the instant compounds in polypropylene.

The base formulation comprises unstabilized, new technology polypropylene (PROFAX 6501, Himont) containing 0.1% by weight of calcium stearate. The test additives are incorporated into the polypropylene by dry blending or, when the additive is a liquid, using a minimum amount of methylene chloride solvent. The solvent is then removed by evaporation under reduced pressure. The stabilized resin formulation is extruded at 80 rpm from a 1 inch (2.54 cm) diameter extruder at 536° F. (280° C.) with a residence time of 45 seconds.

After each of the first and fifth extrusions, the melt flow rate (in grams/10 minutes) is determined by ASTM method D1238 on the pellets obtained from the extruder. The results are given in the table below.

| Additive* | Concentration (% by weight) | Melt Flow after Extrusion | |
|---|---|---|---|
| | | 1 | 5 |
| None | — | 22 | 82 |
| Phosphite 1 | 0.05 | 9.3 | 36 |
| Phosphite 2 | 0.05 | 5.5 | 11 |
| HA 2 | 0.05 | 4.6 | 7.0 |
| Compound of Example 6 | 0.05 | 4.6 | 6.1 |
| AO A | 0.1 | 18 | 26 |
| AO A plus Phosphite 1 | 0.1 0.05 | 14 | 21 |
| AO A plus Phosphite 2 | 0.1 0.05 | 12 | 14 |
| AO A plus HA 1 | 0.1 0.05 | 7.8 | 14 |
| AO A plus Example 4 Compound | 0.1 0.05 | 6.9 | 9.7 |

*AO A is neopentanetetrayl tetrakis(3,5-di-tert-butyl-4-hydroxyhydrocinnamate).
Phosphite 1 is tris(2,4-di-tert-butylphenyl)phosphite.
Phosphite 2 is bis(2,4-di-tert-butylphenyl)pentaerythrityl diphosphite.
HA 1 is N,N-dibenzylhydroxylamine.
HA 2 is N,N-dioctadecylhydroxylamine.

These results show that the instant compounds also provide superior melt flow stabilization to new technology polypropylene during processing compared to the state of the art processing stabilizers when used alone or when used in combination with a phenolic antioxidant.

What is claimed is:

1. A compound of formula I

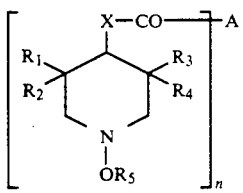

wherein
$R_1$, $R_2$, $R_3$ and $R_4$ are independently hydrogen; a linear or branched alkyl of 1 to 30 carbon atoms; said alkyl optionally terminated with —$OR_6$, —$NR_7R_8$, —$SR_9$, —$COOR_{10}$ or —$CONR_{11}R_{12}$, where $R_6$, $R_7$, $R_8$, $R_9$ and $R_{10}$ are independently alkyl of 1 to 20 carbon atoms or alkenyl of 3 to 18 carbon atoms, and $R_{11}$ and $R_{12}$ are independently hydrogen or the same meaning as $R_6$; or said alkyl interrupted by one or two —O—, —S—, —SO—, —$SO_2$—, —CO—, —COO—, —OCO—, —$CONR_{13}$—, —$NR_{13}CO$— or —$NR_{14}$— where $R_{13}$ and $R_{14}$ have the same meaning as $R_{11}$; alkenyl of 3 to 20 carbon atoms; carbocyclic aryl of 6 to 10 carbon atoms; or said aryl substituted by one to three substiteunts selected from the group consisting of alkyl of 1 to 20 carbon atoms, cycloalkyl of 5 to 12 carbon atoms and phenylalkyl of 7 to 15 carbon atoms;
$R_5$ is hydrogen, alkyl of 1 to 18 carbon atoms, cycloalkyl of 5 to 12 carbon atoms, allyl or benzyl;
X is —O— or —NE—,
E is hydrogen, alkyl of 1 to 18 carbon atoms or cycloalkyl of 5 to 12 carbon atoms,
A is a direct bond; an n-valent linear or branched aliphatic hydrocarbon radical containing 1 to 20 carbon atoms, or said radical interrupted by one or two —O—, —S—, —SO—, —$SO_2$—, —CO—, —COO—, —OCO—, —$CONR_{15}$—, —$NR_{15}CO$— or —$NR_{16}$— where $R_{15}$ and $R_{16}$ have the same meaning as $R_{11}$; an n-valent aromatic or aromatic-aliphatic hydrocarbon of 6 to 30 carbon atoms, or said radical interrupted by one or two —O—, —S—, —SO—, —$SO_2$—, —CO—, —COO—, —OCO—, —$CONR_{17}$, —$NR_{17}CO$— or —$NR_{18}$— where $R_{17}$ and $R_{18}$ have the same meaning as $R_{11}$; and
n is an integer of 1 to 4.

2. A compound according to claim 1 wherein $R_1$, $R_2$, $R_3$ and $R_4$ are independently hydrogen or methyl.

3. A compound according to claim 2 where $R_1$, $R_2$, $R_3$ and $R_4$ are each hydrogen.

4. A compound according to claim 1 where X is —O—.

5. A compound according to claim 1 wherein is 1 to 2.

6. A compound according to claim 1 wherein A is alkyl of 1 to 18 carbon atoms when n is 1; and alkylene of 2 to 12 carbon atoms when n is 2.

7. A compound according to claim 5 wherein A is alkyl of 11 to 17 carbon atoms when n is 1; and alkylene of 2 to 8 carbon atoms when n is 2.

8. A compound according to claim 1 where $R_5$ is hydrogen, allyl or benzyl.

9. A compound according to claim 8 wherein $R_5$ is hydrogen or allyl.

10. The compound according to claim 1 which is 1-hydroxypiperidin-4-yl stearate.

11. The compound according to claim 1 which is bis(1-hydroxypiperidin-4-yl) sebacate.

12. The compound according to claim 1 which is
(a) bis(1-allyoxy-3,5-dimethylpiperidin-4-yl) sebacate;
(b) bis(1-allyloxypiperidin-4-yl) sebacate;
(c) 1-allyloxypiperidin-4-yl stearate;
(d) bis(1-benzyloxypiperidin-4-yl) sebacate;
(e) 1-benzyloxypiperidin-4-yl) stearate; or
(f) 4-(N-n-butyl-N-stearoylamino)-1-hydroxypiperidine.

* * * * *